United States Patent [19]
Jackson et al.

[11] 4,123,460
[45] Oct. 31, 1978

[54] PROCESS FOR THE PRODUCTION OF MONOHALOACETYLHALIDES

[75] Inventors: Barry Jackson; Christoph Zinsstag, both of Visp, Switzerland

[73] Assignee: Lonza, Ltd., Gambel, Switzerland

[21] Appl. No.: 837,437

[22] Filed: Sep. 28, 1977

[30] Foreign Application Priority Data

Sep. 28, 1976 [CH] Switzerland ............... 12234/76

[51] Int. Cl.$^2$ ................................................. C07C 51/58
[52] U.S. Cl. .............................. 260/544 D; 260/544 Y
[58] Field of Search ............ 260/544 Y, 544 L, 544 D

[56] References Cited

U.S. PATENT DOCUMENTS 3,883,589  5/1975  Gash et al. ........................ 260/544 Y Primary Examiner—Gerald A. Schwartz Attorney, Agent, or Firm—Fisher, Christen & Sabol

[57] ABSTRACT

A process for the production of a monohaloacetylhalide characterized in that a ketene is reacted with a halogen in the presence of a diester of phosphonic acid of the formula:

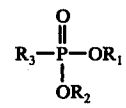

wherein $R_1$, $R_2$ and $R_3$ are the same or different alkyl or aryl, or $R_1$ and $R_2$ are the same or different alkyl or aryl and $R_3$ is —COOR or —CH$_2$COOR, wherein R is alkyl or aryl. The diester is a solvent which impedes or prevents the formation of polyhaloacylhalides and which keeps the formation of acylhalides to a minimum.

9 Claims, No Drawings

PROCESS FOR THE PRODUCTION OF MONOHALOACETYLHALIDES

BACKGROUND OF THE INVENTION

1. Field of This Invention

This invention relates to a process for the production of a monohaloacetylhalide by the halogenation of a ketene in the liquid phase. This invention particularly relates to the halogenation of a ketene in the presence of a solvent, which impedes or prevents the formation of polyhaloacylhalides and keeps the formation of acylhalides to a minimum.

2. Prior Art

The halogenation of ketene in the liquid phase is known. However the known methods for carrying out such conversion lead to the formation of monohaloacetylhalides which are contaminated to a considerable degree with dihaloacetylhalides and polyhalogenated by-products. In the known processes, solvents such as alkyl-acetates (Brit. Pat. No. 782,773), $SO_2$ (U.S. Pat. No. 2,889,365), alicyclic carbonates, alkoxyalkylesters, glycolesters (Germ. OS No. 2,247,764), sulfones (U.S. Pat. No. 3,882,173), phosphate esters (U.S. Pat. No. 3,883,589) or lactones (Germ. OS No. 2,247,765) have been used. Most of such solvents have the common disadvantage that their use leads to the formation of a considerable quantity of dihaloacetylhalide along with the desirable monohaloacetylhalide product. Such dihalogen derivataives have no commercial value and, moreover, their separation from the monohalogen derivatives is too expensive and time consuming. Thus, for example, dichloroacetylchloride has a boiling point of almost 107° C., while monochloroacetylchloride has a boiling point of 105° C. Because the boiling points are very close together, it is difficult to separate these two compounds. An expensive and unprofitable separation must follow the halogenation process whenever the halogenation is carried out in the known solvents used for this purpose. When phosphate esters lactones are used as solvents, only small quantities of undesirable by-product are obtained.

BROAD DESCRIPTION OF THIS INVENTION

An object of this invention is to provide a process for the production of a monohaloacetylhalides by the halogenation of a ketene in the liquid phase. Another object of this invention is to provide a process for the halogenation of a ketene in the presence of a solvent, which impedes or prevents the formation of polyhaloacylhalides and keeps the formation of acylhalides to a minimum. Other objects and advantages of this invention are set out herein or are obvious herefrom to one ordinarily skilled in the pertinent art.

The objects and advantages of this ivention are obtained by the process of this invention.

The monohaloacetylhalides, produced by the process of this invention, are valuable intermediate products for the production of α-haloacetonilides and other products which are useable as herbicides - contrary thereto are the corresponding di- and trihaloacetylhalides which have no commercial importance. In other words, mixed with the commercially valuable monohaloacetylhalides they merely represent a diluent, which reduces the effectiveness of the former. The fact that all chloroacetylchlorides presently obtainable on the market are contaminated with considerable quantities of dichloroacetylchloride (the dichloroacetychloride content in some cases being up to 6 percent) points out the importance of this problem.

The process of this invention for the production of monohaloacylhalides by halogenation of ketenes in the liquid phase is characterized in that a ketene is reacted with a halogen in the presence of a diester of phosphoric acid of the formula:

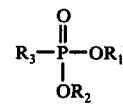

wherein $R_1$, $R_2$ and $R_3$ are the same or different alkyl or aryl, or $R_1$ and $R_2$ are the same or different alkyl or aryl and $R_3$ is —COOR or —CH$_2$COOR, wherein R is alkyl or aryl.

Preferably diesters of the phosphoric acid are used wherein $R_1$, and $R_2$ and $R_3$ are the same or different and are alkyl radicals having 1 to 6 carbon atoms. Such compounds are, for example, dimethylmethanephosphonate and diethylethanephosphonate. Other preferred diesters of the phosphonic acid are those wherein $R_1$ and $R_2$ are alkyl having 1 to 6 carbon atoms and $R_3$ is —COOR or —CH$_2$COOR, wherein R is alkyl having 1 to 6 carbon atoms. Such compounds are, for example, diethoxyphosphonic formic acid methyl ester and diethoxyphosphonic acetic acid ethyl ester.

The process of this invention includes the halogenation of ketene (CH$_2$=C=O), as well as the halogenation of substituted ketenes (R$_4$CH=C=O and R$_4$R$_5$C=C=O, wherein R$_4$ and R$_5$ can be the same or different and are aryl or alkyl having 1 to 6 carbon atoms), such as, methylketene, dimethylketene, ethylketene, diethylketene, phenylketene, diphenylketene, etc.

In the process of this invention, the ketene and the halogen are introduced into a solvent medium consisting of a diester of the phosphonic acid, or containing an ester of the phosphonic acid, wherein they react while forming monohaloacetylhalides. The monohaloacetylhalides can be separated from the reaction medium using traditional methods, for example, distillation preferably at reduced pressure. The process of this invention can be carried out on a continuous or intermittent basis. The process conditions at which the reaction is carried out are not critical, but preferably they should be kept within certain limiting values in order to keep the yield of monohaloaceylhalides as high as possible. Essentially it is only necessary that the diesters of the phosphonic acid are liquid under the prevailing reaction conditions. Because of practical considerations, the reaction normally is carried out, however, at a temperature from about −50° to 100° C. and under a pressure from about 50 torr to about 2 kg/cm². In most cases, however, it is preferable to operate at a temperature between about 0° and about +50° C. and at a pressure between about 100 and 760 torr. The advantages of this invention can be achieved to a higher degree whenever the molar ratio of halogen to ketene is kept between about 0.8 to 1 and about 2.0 to 1.

The term "halogen" or "halogen compound" or "halogenation agent" in this specification, including the claims, comprises chlorine, bromine, iodine and halogen halides, such as, iodine monochloride, iodine bromochloride, bromine monochloride, iodine monobromide, iodine tribromide and iodine trichloride.

Examples of useful alkyls having 1 to 6 carbon atoms (as used herein) are methyl, ethyl, n-propyl, isopropyl, n-butyl, isobutyl, sec.-butyl, tert.-butyl, n-amyl, 2-methyl-1-butyl, 2-pentyl, 3-methyl-2-butyl, isoamyl, 3-pentyl, 2-methyl-1-pentyl, n-hexyl, 3-methyl-1-pentyl, isohexyl, 2-ethyl-1-butyl, 2,3-dimethyl-1-butyl, 2-hexyl, 3-hexyl and 3-methyl-2-pentyl.

Examples of useful aryls and alkaryls (as used herein) are phenyl, benzyl and naphthyl.

DETAILED DESCRIPTION OF THIS INVENTION

The subsequent specific embodiments illustrate this invention. In the examples and the description, quantitative data is always in parts by weight, if no other basis is specified.

EXAMPLE I

A suitable reaction vessel, equipped with a stirrer, gas outlet and temperature indicator, was charged with 116 gm. of diethylethanephosphonate. Then an equimolar quantity of ketene and chlorine (a halogen) was introduced into the reaction mix, and kept at about 10° C., at a constant mixing speed (0.348 mol/hr) while stirring continuously and at atmosphoric pressure. After about 3 hours the supply of the reaction participants was exhausted. Upon completion of the reaction, the ratio of solvent to the sum of solvent and product was about 0.5. The reaction mix contained only the solvent, chloroacetylchloride, some acetylchloride and a diminutive quantity of dichloroacetylchloride. After distillation of the reaction mix at 11 mm Hg for the separation of pure chloroacetylchloride, the yield of chloroacetylchloride was determined to be 78 percent with 4.5 percent of acetylchloride and 0.2 percent of dichloroacetylchloride.

EXAMPLES 2 to 4

The following table contains the data for Examples 2 to 4. These examples were carried out as in Example 1, with the exception that other diesters of phosphonic acid were used as the solvent.

a result, the profitability of the process is greatly improved. From the high percentages of recaptured solvent, it is furthermore seen that the favorable effect achieved by such solvent rests upon the specific characteristics of the substance of the chemical structure characterizing them.

The favorable results characterizing the process of this invention is also obtained when other representatives of the halogenation agents of this invention are used instead of the halogenation agents used in the Examples. Bromine can be fed into the reaction system as a liquid in combination or in solution, into the diester of phosphonic acid, or as a gas which is introduced below the surface of the reaction mix. Whenever iodine monochloride is used as the halogenation agent, it can be fed into the reactor by dissolving it in the solvent and by feeding the solution obtained thereby into the reaction system.

What is claimed is:

1. Process for the production of a monohaloacetylhalide characterized in that (a) $CH_2{=}C{=}O$, $R_4CH{=}C{=}O$ or $R_4 R_5 C{=}C{=}O$, wherein $R_4$ and $R_5$ can be the same or different and are aryl or alkyl having 1 to 6 carbon atoms, is reacted with (b) a halogen in the presence of a diester of phosphonic acid of the formula:

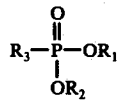

wherein $R_1$, $R_2$ and $R_3$ are the same or different alkyl or aryl, or $R_1$ and $R_2$ are the same or different alkyl or aryl and $R_3$ is —COOR or —CH$_2$COOR, wherein R is alkyl or aryl, the reaction being conducted in the liquid phase at a temperature between about −50° and about 100° C.

2. Process as claimed in claim 1 wherein, in said phosphonic acid of formula I, $R_1$, $R_2$ and $R_3$ are the same or different alkyl having 1 to 6 carbon atoms.

3. Process as claimed in claim 1 wherein, in said diester of phosphonic acid formula I, $R_1$ and $R_2$ are the same

TABLE

| SOLVENT | | YIELD, PERCENT | | | RECAPTURED SOLVENT, PERCENT |
|---|---|---|---|---|---|
| | | AC | CAC | DCAC | |
| $CH_3{-}\underset{\underset{OCH_3}{\mid}}{\overset{\overset{O}{\parallel}}{P}}{-}OCH_3$ | diethylmethane phosphonate | 12.7 | 73.2 | 0.3 | 85 |
| $C_2H_5O{-}\overset{\overset{O}{\parallel}}{C}{-}CH_2{-}\underset{\underset{OC_2H_5}{\mid}}{\overset{\overset{O}{\parallel}}{P}}{-}OC_2H_5$ | phosponoacetic acid triethyl ester | 6.0 | 83.7 | 0.3 | 92 |
| $CH_3O{-}\overset{\overset{O}{\parallel}}{C}{-}\underset{\underset{OC_2H_5}{\mid}}{\overset{\overset{O}{\parallel}}{P}}{-}OC_2H_5$ | diethoxyphosphonoformic acid methylester | 6.0 | 89.2 | 0.3 | 93 |
| $C_4H_9{-}\underset{\underset{OC_4H_9}{\mid}}{\overset{\overset{O}{\parallel}}{P}}{-}OC_4H_9$ | dibutylbutane phosphonate | 6.6 | 85.2 | 0.1 | 96 |

Notes:
AC = acetylchloride;
CAC = chloroacetylchloride;
DCAC = dichloroacetylchloride.

The improvement achieved by the use of the solvents of this invention also finds its expression in the fact that the percentage of recaptured solvents for returning to circulation in the process is mostly above 90 percent. As or different alkyl having 1 to 6 carbon atoms and $R_3$ is —COOR or —CH$_2$COOR, wherein R is alkyl having 1 to 6 carbon atoms.

4. Process as claimed in claim 1 wherein said diester of phosphonic acid is dimethylethane phosphonate, diethoxyphosphonoacetic acid ethyl ester or dibutylbutane phosphonate.

5. Process as claimed in claim 1 wherein said reaction is conducted at a pressure between about 50 torr and about 2kg/cm$^2$.

6. Process as claimed in claim 1 wherein the molar ratio of halogen to ketene is between about 0.8 to 1 and about 2.0 to 1.

7. Process as claimed in claim 1 wherein said halogen is chlorine, bromine, iodine or a halogen halide.

8. Process as claimed in claim 1 wherein R$_4$CH=C=O is methylketene, ethylketene or phenylketene.

9. Process as claimed in claim 1 wherein R$_4$R$_5$C=C=O is dimethylketene, diethylketene or diphenylketene.

* * * * *

UNITED STATES PATENT OFFICE
CERTIFICATE OF CORRECTION

Patent No. 4,123,460　　　　　　　　Dated October 31, 1978

Inventor(s) Barry Jackson and Christoph Zinsstag

It is certified that error appears in the above-identified patent and that said Letters Patent are hereby corrected as shown below:

In the heading, item [73], cancel "Gambel," and insert therefor --Gampel,--.

Signed and Sealed this

Twenty-seventh Day of February 1979

[SEAL]

Attest:

RUTH C. MASON
Attesting Officer

DONALD W. BANNER
Commissioner of Patents and Trademarks